United States Patent
Younis

(10) Patent No.: US 12,253,522 B2
(45) Date of Patent: Mar. 18, 2025

(54) METHOD FOR TREATING A CANCER BASED ON INFLAMMATORY SUBTYPE THEREOF

(71) Applicant: Rania H. Younis, Ellicott City, MD (US)

(72) Inventor: Rania H. Younis, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 17/379,909

(22) Filed: Jul. 19, 2021

(65) Prior Publication Data

US 2022/0018844 A1    Jan. 20, 2022

Related U.S. Application Data

(60) Provisional application No. 63/053,803, filed on Jul. 20, 2020.

(51) Int. Cl.
*G01N 33/574* (2006.01)
*A61K 45/06* (2006.01)
*G01N 33/543* (2006.01)

(52) U.S. Cl.
CPC ....... *G01N 33/57484* (2013.01); *A61K 45/06* (2013.01); *G01N 33/543* (2013.01); *G01N 2333/70503* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 10,973,843 B2 * | 4/2021 | Younis | G01N 33/57484 |
| 2019/0134195 A1 * | 5/2019 | Jones | A61P 31/20 |
| 2020/0216908 A1 * | 7/2020 | Lai-Goldman | C12Q 1/686 |
| 2021/0008135 A1 * | 1/2021 | Gansert | A61K 35/763 |

OTHER PUBLICATIONS

Derakhshandeh et al., Oncotarget, 9(13):11126-11144, 2018.*
Younis et al., Cancer Res., 77(13_Supplement):3672 2017.*
Younis et al., Frontiers in Immunology, 12:596646; doi: 10.3389. fimmu.2021.596646, Mar. 11, 2021.*

* cited by examiner

*Primary Examiner* — Marianne P Allen
(74) *Attorney, Agent, or Firm* — Benjamin Aaron Adler

(57) ABSTRACT

Provided herein is a method for treating a cancer in a subject by quantitating the concentration of a soluble form of Semaphorin 4D (sSema4D) in a blood sample obtained from the subject and administering an immunotherapy when the blood concentration of sSema4D is below a threshold value of 155 ng/ml. Also provided is a method for determining the continued susceptibility of a tumor tissue to immunotherapy in a subject by identifying the inflammatory subtype of the tumor tissue from a blood sample from the subject and administering immunotherapy over at least one interval as long as the tumor tissue exhibits an inflamed subtype.

5 Claims, 13 Drawing Sheets

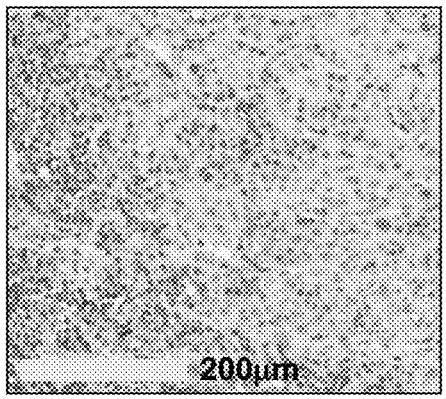
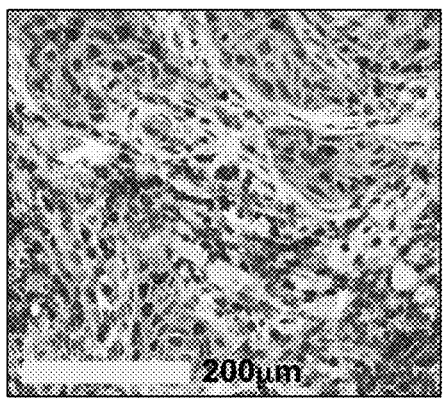
FIG. 2A  FIG. 2B
HIS-INF
n=50
(52%)
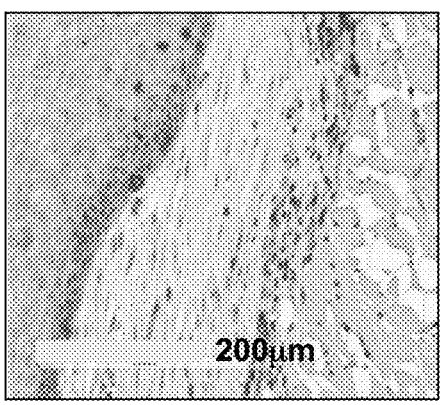
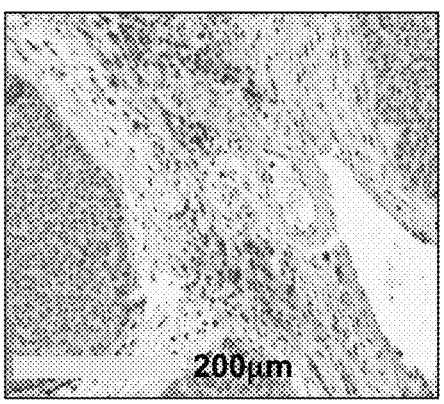
FIG. 2C  FIG. 2D
HIS-IE
n=38
(40%)
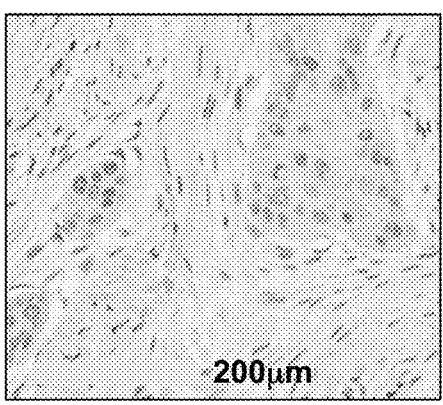
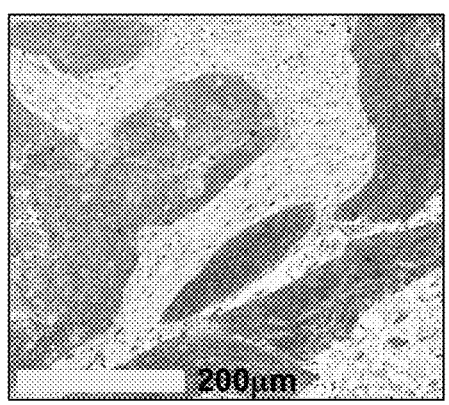
FIG. 2E  FIG. 2F
HIS-ID
n=8
(8%)

METHOD FOR TREATING A CANCER BASED ON INFLAMMATORY SUBTYPE THEREOF

CROSS-REFERENCE TO RELATED APPLICATIONS

This non-provisional application claims benefit of priority under 35 U.S.C. § 119(e) of provisional application U.S. Ser. No. 63/053,803, filed Jul. 20, 2020, which is hereby incorporated by reference in its entirety.

BACKGROUND OF THE INVENTION

Field of the Invention

The present invention is in the field of cancer diagnosis and prognosis. More specifically, the present invention relates to detecting and measuring soluble biomarkers for a cancer as an indicator for immunotherapy.

Description of the Related Art

Head and neck squamous cell carcinoma (HNSCC) is a devastating malignancy that occurs in close proximity to vital structures. A projection for the year 2020 estimated that 53,260 new cases and 10,750 annual deaths of oral and pharyngeal SCC will occur in the US (1). Surgical excision remains the first line of treatment for oral cavity cancer. Depending on the disease presentation and pathological findings, other therapies are often required including radiotherapy as a single or adjuvant option, chemotherapy, targeted agents, and immunotherapy as the most recent therapeutic advent (2). The overall 5-year survival rate is 65% with an average 6-10 month survival rate for platinum resistant patients (3). Several studies have described HNSCC as an immune suppressive tumor (4, 5). The recent advent of immunotherapy showed unprecedented improvement in overall response of advanced stage malignancy (2).

Semaphorin 4D (CD 100, Sema4D) is an immune biomarker that belongs to the fourth group of the Semaphorin family, which shares a conserved N-terminal domain (the 'Sema' domain) having highly conserved cysteine residues (20). Sema4D is expressed in white blood cells of lymphoid and myeloid origins (21-25). Sema4D expressed in activated T cells binds its low affinity receptor CD72 on B cells, or on antigen presenting cells, thereby activating humoral or T cell-mediated immunity, respectively (26, 27). Sema4D is a transmembrane glycoprotein that can function in the bound or soluble form. MT1-MMP and ADAM17 have been implicated in Sema4D proteolytic cleavage and shedding (28-30). The soluble form of Sema4D (sSema4D) inhibits spontaneous and cytokine-induced migration in myeloid cells (22). In the tumor microenvironment HNSCC-derived sSema4D was shown to induce immune suppression through upregulation of myeloid derived suppressor cells (MDSC) (5), as well as the increase of extracellular collagen deposition by fibroblasts (32).

Expression of Sema4D has been described in tumor cells (TC) of several malignancies including HNSCC and by tumor infiltrating immune cells (IC), including tumor associated macrophages (TAMs) (32, 33). Sema4D also promotes tumor migration and invasion through Rho activation, microtubule organization and epithelial mesenchymal transition (34) and has been associated with overall poor prognosis in sarcomas and cutaneous SCC (35, 36). Importantly, sSema4D is present in the peripheral blood of HNSCC patients, and other pathologic conditions including heart failure, autoimmunity and allergy (37-39).

The status of the peritumoral stromal inflammatory profile (PTSIP) has proved to be an important parameter to predict patient response to immunotherapy. In the current standard of care for advanced HNSCC, immunotherapy administration is recommended for platinum resistant patients. This requires assessment of PD-L1 expression levels. Data obtained from initial biopsies of the primary tumor tissue are however not representative of the evolving PTSIP dynamics as the tumor progresses and advances immediately prior to treatment. Surgical tissue biopsy is however not an option in many circumstances, particularly in platinum refractory advanced HNSCC patients. The oncologist therefore monitors the response to immunotherapy using a system of immune response evaluation criteria in solid tumors (iRECIST) by employing Computerized tomography (CT) and/or positron emission tomography scan (PET); expensive technologies that must be employed every 9 weeks to measure the relative change in tumor size (CT) and the metabolic activity of the lesion (PET). Currently, there are no technologies available to monitor the underlying dynamics of PTSIP as the tumor disseminates and advances.

Overall, there is a deficiency in the art for cost-effective, non-invasive screening methods to evaluate tumor tissue immune profiles as an indicator of the suitability of immunotherapy. The present invention fulfills this longstanding need and desire in the art.

SUMMARY OF THE INVENTION

The present invention is directed to a method for treating a cancer in a subject in need thereof. In the method a blood sample is obtained from the subject and a concentration of a soluble form of Semaphorin 4D (sSema4D) is quantitated therein. An immunotherapy is administered to the subject when the concentration of sSema4D is below a threshold value.

The present invention is directed to a related method further comprising repeating the obtaining step and the quantitating step during at least one interval and administering the immunotherapy if the concentration of the sSema4D after each interval remains below the threshold value. The present invention is directed to another related method further comprising repeating the obtaining step and the quantitating step during at least one interval and discontinuing the immunotherapy if the concentration of sSema4D after each interval is equal to or greater than the threshold value. The present invention is directed to another related method further comprising repeating the obtaining step and the quantitating step during at least one interval and administering at least one Sema4D inhibitor or a combination of the at least one Sema4D inhibitor and the immunotherapy or at least one stromal myofibroblast inhibitor or a combination of a stromal myofibroblast inhibitor and the immunotherapy if the concentration of sSema4D after each interval is equal to or greater than the threshold value.

The present invention is also directed to a method for treating a cancer in a subject in need thereof. In the method a blood sample is obtained from the subject and a concentration of a soluble form of Semaphorin 4D (sSema4D) is measured therein. An immunotherapy is administered to the subject when the concentration of the sSema4D is below 155 ng/ml. The obtaining step, measuring step and administering step are repeating during at least one interval The present invention is directed further to a method for determining the continued susceptibility of a tumor tissue to immunotherapy in a subject in need thereof. In the method an inflammatory subtype of the tumor tissue is identified from a first blood sample obtained from the subject. An immunotherapy is administered to the subject when the inflammatory subtype is identified as an inflamed subtype. At least a second blood sample is obtained from the subject during at least one interval after administering the immunotherapy and the inflammatory subtype is identified, wherein, if the inflammatory subtype is the inflamed subtype, the tumor tissue continues to be susceptible to the immunotherapy. The present invention is directed to a related method further comprising repeating the obtaining step, the measuring step, the administering step, and the repeating step, if the inflammatory subtype at the repeating step is identified as inflamed.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 2A-2F show representative immunohistochemical (IHC) staining defining the HIS subtypes in HNSCC. FIG. 2A shows HIS-INF (histological inflammatory stroma subtype-inflamed) staining of OSCC tumor (OSCC5-18-03-INF) demonstrating IC infiltrate into the core of the tumor islands. FIG. 2B shows HIS-INF staining of OSCC tumor (OSCC-18-13 INF) demonstrating IC infiltrate into the core of the tumor islands. FIG. 2C shows HIS-IE (histological inflammatory stroma subtype-immune excluded) staining of OSCC tumor (OSCC9-18-22-IE) showing IC excluded from tumor island by a rim of peri-tumoral stromal fibrosis (PTSF). FIG. 2D shows HIS-IE staining of OPSCC tumor (OPSCC7-18-08-IE) showing IC excluded from tumor island by a fibromyxoid (FMX) rim. FIG. 2E shows HIS-ID ((histological inflammatory stroma subtype-immune desert) staining in OSCC tumors (OSCC-19-33-ID) showing cold non-inflamed fibrotic dense stroma deserted of IC. FIG. 2F shows HIS-ID staining in OSCC tumors (OSCC 2018-33-ID) showing cold non-inflamed fibrotic dense stroma deserted of IC.

FIG. 3A shows PCA analysis of the HIS-IE and HIS-INF. FIG. 3B shows a heat map of the refined 6 IFN-γ-signature in representative HIS tumors. FIG. 3C shows a heat map illustrating final IFN-γ 18 gene signature between grouped cases of the three HIS subtypes (SCC 5&6 (INF), 7&8 (IE), 9&10 (ID)).

FIG. 4A shows a heat map illustrating individual tumors using IFN-γ expanded 16 genes signature. FIG. 4B shows a heat map of expanded IFN-γ 16 genes signature between grouped cases of the three HIS subtypes (SCC 5&6 (INF), 7 and 8 (IE), 9 and 10 (ID)). INF; inflamed, IE; immune excluded, ID; immune deserted.

FIG. 5A shows sSema4D levels in plasma of AI/A/CI (Autoimmune disease/Asthma/chronic inflammation-osteoarthritis) patients.

FIG. 5B shows sSema4D in RA versus other collagenous AI other collagenous AI conditions (other Col AI).

FIG. 6A shows sSema4D levels in plasma in HNSCC, CI (AI/A/CI) and HD (healthy donors). FIG. 6B shows sSema4D in relation to the HIS subtypes (INF, IE, ID). FIG. 6C shows that sSema4D levels correlate with Sema4D in tumor cells

FIG. 9A is a trend plot of immune cell type relative to total tumor infiltrating lymphocytes (TILs) in LsS4D versus HsS4D. FIG. 9B is a trend plot analysis of immune-oncologic signaling pathways in LsS4D versus HsS4D.

DETAILED DESCRIPTION OF THE PRESENT INVENTION

Figure 1:
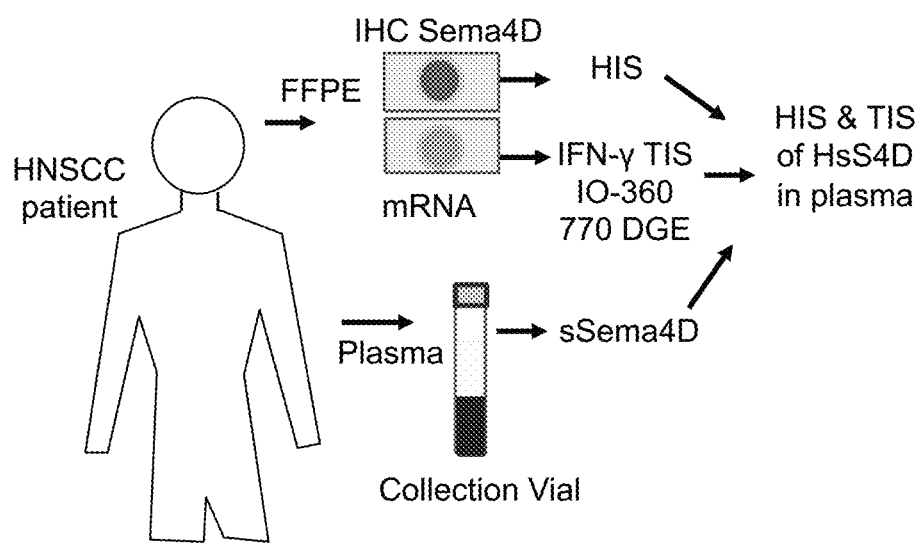
FIG. 1 is an experimental outline and workflow for analysis of tumor tissue and peripheral blood from HNSCC patients obtained at the same time point for real time analysis of sSema4D in plasma in correlation to HIS and DGE.

For convenience, before further description of the present invention, certain terms employed in the specification, examples and appended claims are collected herein. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, components, method steps, and/or methods of the invention. It is contemplated that any composition, component or method described herein can be implemented with respect to any other composition, component or method described herein.

The term "or" in the claims refers to "and/or" unless explicitly indicated to refer to alternatives only or the alternatives are mutually exclusive, although the disclosure supports a definition that refers to only alternatives and "and/or".

The terms "comprise" and "comprising" are used in the inclusive, open sense, meaning that additional elements may be included.

The term "including" is used herein to mean "including, but not limited to". "Including" and "including but not limited to" are used interchangeably.

As used herein, the term "about" refers to a numeric value, including, for example, whole numbers, fractions, and percentages, whether or not explicitly indicated. The term "about" generally refers to a range of numerical values (e.g., ±5-10% of the recited value) that one of ordinary skill in the art would consider equivalent to the recited value (e.g., having the same function or result). In some instances, the term "about" may include numerical values that are rounded to the nearest significant figure. For example, an interval of about 3 weeks to about 9 weeks encompasses 2.7 weeks to 10 weeks.

As used herein, the term "standard immunotherapy" refers to those immunotherapeutic processes known or common in the art, particularly, but not limited to, in the treatment of cancer.

In one embodiment of the present invention there is provided a method for treating a cancer in a subject in need thereof, comprising the steps of a) obtaining a blood sample from the subject; b) quantitating a concentration of a soluble form of Semaphorin 4D (sSema4D) in the blood sample; and c) administering an immunotherapy to the subject when the concentration of sSema4D is below a threshold value.

Further to this embodiment in one aspect thereof the method comprises repeating steps a to b during at least one interval and administering the immunotherapy, if the concentration of the sSema4D after each interval remains below the threshold value. In this aspect the interval may be about every 3 weeks to about every 9 weeks. Further to this embodiment in another aspect thereof the method comprises repeating steps a to b during at least one interval; and discontinuing the immunotherapy, if the concentration of sSema4D after each interval is equal to or greater than the threshold value. Further to this embodiment in yet another aspect thereof the method comprises repeating steps a to b during at least one interval; and administering at least one Sema4D inhibitor or a combination of the at least one Sema4D inhibitor and the immunotherapy or at least one stromal myofibroblast inhibitor or a combination of the at least one stromal myofibroblast inhibitor and the immunotherapy, if the concentration of sSema4D after each interval is equal to or greater than the threshold value. In this aspect, the cancer may be resistant to treatment with platinum containing therapeutics.

In all embodiments and aspects thereof the quantitating step may comprise performing an ELISA on the blood sample. Also, the threshold value for the concentration of sSema4D may be 155 ng/ml. In addition the cancer is a head and neck squamous cell carcinoma.

In another embodiment of the present invention there is provided a method for treating a cancer in a subject in need thereof, comprising the steps of a) obtaining a blood sample from the subject; b) measuring a concentration of a soluble form of Semaphorin 4D (sSema4D) in the blood sample; c) administering an immunotherapy to the subject when the concentration of the sSema4D is below 155 ng/ml; and d) repeating steps a to c during at least one interval.

In this embodiment the immunotherapy may be discontinued if the concentration of the sSema4D measured after the interval is equal to or greater than the 155 ng/ml. Also in this embodiment the cancer may be a head and neck squamous cell carcinoma.

In yet another embodiment of the present invention there is provided a method for determining the continued susceptibility of a tumor tissue to immunotherapy in a subject in need thereof, comprising a) identifying an inflammatory subtype of the tumor tissue from a first blood sample obtained from the subject; b) administering an immunotherapy to the subject when the inflammatory subtype is identified as an inflamed subtype; c) obtaining at least a second blood sample from the subject during at least one interval after administering the immunotherapy; d) identifying the inflammatory subtype wherein, if the inflammatory subtype is the inflamed subtype, the tumor tissue continues to be susceptible to the immunotherapy. In a further embodiment the method comprises repeating steps a) to d) if the inflammatory subtype at step d) is inflamed.

In both embodiments the steps of identifying the inflammatory subtype each may comprise quantifying a concentration of a soluble form of Semaphorin 4D (sSema4D) in the blood type; and comparing the concentration to a threshold value of 155 ng/ml sSema4D; wherein if the concentration in the blood sample is less than the threshold value, the inflammatory subtype is inflamed. Also in both embodiments in step c the interval may be about every 3 weeks to about every 9 weeks. In addition the tumor tissue may be a head and neck squamous cell carcinoma.

In both embodiments the method may comprise obtaining the first blood sample from the subject; measuring a concentration of the sSema4D in the blood sample; administering the immunotherapy to the subject when the concentration of the sSema4D is below 155 ng/ml thereby identifying the inflammatory subtype as an inflamed subtype; c) obtaining at least the second blood sample from the subject during the at least one interval after administering the immunotherapy; d) measuring the concentration of the sSema4D, wherein, if the concentration remains below the 155 ng/ml, the tumor tissue continues to be susceptible to the immunotherapy. Also, the measuring step d may comprise performing an ELISA on the blood sample.

Provided herein are methods for the treatment of cancer in a subject based on the inflammatory subtype of the cancer or tumor tissue. The cancer may be a solid cancer, such as a head and neck squamous cell carcinoma. Inflammatory subtype is determined by assaying a biological sample, such as, a blood sample, for the level or concentration of a soluble form of Semaphorin 4D (sSema4D). The assay may be performed via ELISA as is well-known and standard in the art.

The cancer or tumor tissue is susceptible to immunotherapy, such as a standard immunotherapy, when the concentration of the sSema4D is less than a threshold value or level of 155 ng/ml, which indicates an inflamed subtype. One of ordinary skill in the art is well able to design an immunotherapeutic regimen, including separate doses and overall dosage for the subject based on criteria such as, but not limited to, type and stage of the cancer, for example, whether the cancer is drug resistant or has acquired drug resistance, previous treatments and results, if any, age and sex of the subject, and overall health of the subject when diagnosed. The immunotherapeutic regimen may be administered at any suitable interval, for example, but not limited to, about 3 weeks to about 9 weeks and for a suitable number of intervals depending on the efficacy of the immunotherapy.

Also provided are methods of determining whether a cancer or tumor tissue continues to be susceptible to immunotherapy. A blood sample may be obtained after each interval of immunotherapy and the concentration of sSema4D measured as described herein. If the concentration continues to stay below the 155 ng/ml threshold value or level, the cancer or cancer cells or tumor tissue remains susceptible to immunotherapy. If the sSema4D concentration is equal to or greater than the 155 ng/ml threshold value, the immunotherapy is discontinued as the cancer or cancer cells or tumor tissue is no longer susceptible to the immunotherapy. Alternatively, if the sSema4D concentration is equal to or greater than the 155 ng/ml threshold value the cancer may be treated with at least one inhibitor of Sema4D or at least one inhibitor of stromal myofibroblasts or a combination of the inhibitor(s) and the immunotherapy, such as a standard immunotherapy. Such inhibitors are known in the art. This is useful to provide an alternative therapy for a cancer that is resistant to platinum based drugs, chemotherapeutic agents or other therapies.

The following examples are given for the purpose of illustrating various embodiments of the invention and are not meant to limit the present invention in any fashion.

Example 1

Paired Tumor Tissue and Plasma of HNSCC Patients

Under an Institutional Review Board (IRB) approved protocol at the University of Maryland School of Medicine (UMSOM) (HP-00073603), paired blood samples and whole excision tumor tissue were collected prospectively at the day of surgery from 104 HNSCC upon informed patient consent. The main inclusion criteria was primary tumors resected by surgery as the initial line of treatment. The blood was drawn pre-operatively prior to the planned surgical excision and processed to obtain plasma within 2 hours of collection. Plasma from 51 patients with chronic pathological conditions served as controls. These included patients with autoimmune conditions (31 cases), allergy (10 cases) and osteoarthritis (10 cases) and 11 samples from healthy donors were collected retrospectively under an approved UMSOM IRB protocol HP-00074877. An additional 20 healthy donor plasma samples were purchased from Innovative Research (Novi, MI). All blood samples were processed to obtain plasma in sodium heparin tubes (BD Vacutainer glass tubes Medex Supply, NY; cat #366480)

Sema4D ELISA

Sema4D concentration in the plasma was determined using direct ELISA as previously described (5). Briefly, Immulon 4 HBX microtiter plates (Thermo Scientific, Waltham, Mass.) were coated with undiluted plasma, washed with ELISA washing buffer, then incubated with anti-human CD100 antibody (clone: 133-106; Invitrogen, eBioscience, CA; cat #14-1009-82) overnight. Then followed by Goat anti-mouse IgM-Heavy chain, HRP conjugate secondary antibody (Invitrogen USA, IL; cat. #62-6820), detection with TMB (Biolegend, CA; cat #421101) and Stop Solution (Biolegend, CA; cat #77316). The concentrations of Sema4D were calculated using the standard curve established using recombinant Sema4D (catalog no. 310-29) (Peprotech, RockyHill, NJ). The detection limit was 3.1 ng/mL-1000 ng/ml. Plates were read at 450 nm wavelength using BioTek Epoch microplate spectrophotometer.

Immunohistochemistry

For Sema4D staining, the avidin-biotin complex (ABC) technique was used following Vectastain elite ABC kit (PK-6102, mouse IgG) (Vector Laboratories, CA). Briefly, FFPE tissue sections were deparaffinized, then rehydrated in graded ethanol, treated with Tris-EDTA buffer for antigen retrieval, and quenched in hydrogen peroxide to block endogenous peroxidase. Tissue sections were blocked with 2.5% normal plasma, incubated overnight at 40 C with anti-Sema4D antibody (clone 30/CD100; Catalog no. 610670) (BD Transduction Laboratories), followed by biotinylated secondary antibody (catalog no. BA-9200), then the ABC reagent. Primary antibody was omitted for negative control. Diaminobenzidine (SK-4105) was used as chromogen and counterstained with Mayer's hematoxylin (Sigma-Aldrich Corp.). PD-L1 staining (clone 28-8, catalog no. ab205921, Abcam), was used to stain the HNSCC sections according to Abcam IHC protocol. Universal HIER antigen retrieval reagent catalog # (ab208572), Rabbit specific IHC polymer detection kit HRP/DAB catalog # (ab209101) Amplifier and Detector, and DAB substrate kit catalog # (ab64238) were used from Abcam according to their PD-L1 IHC protocol.

The Sema4D and PD-L1 labeling index (LI) reflecting the intensity and extent of staining in the TC and the IC was defined semi quantitatively using intensity and percentage of staining as (0, 1, 2, and 3). (0) was negative, (1) focal or diffuse weak staining, (2) focal strong positivity≤25%, and (3) for diffuse strong positivity>25%. The combined positive score (CPS) counted for both TC and IC positivity. The immunohistochemical (IHC) score standardization was carried by the surgical pathologists (JP, RC, RY), then the 104 HNSCC samples were scored by (RY & RC). Discordant scores were adjudicated by JP. Slides were scanned using Leica biosystem scanscope. Histological features including extent of peritumoral stromal fibrosis, the extent of inflammation taking into consideration the size of the tumor islands in relation to the number of immune (IC) infiltrate. The Histological inflammatory subtype (HIS) was scored according to Sema4D positive IC infiltrate into the tumor core, IC excluded by thin peritumoral fibrous rim or only at the tumor margin, or no IC in stroma, was carried using the Aperio Imagescope.

RNA Extraction and nSolver Analysis

For RNA extraction, 3 to 5 unstained, 5 mm thick, FFPE tissue sections from 10 cases were used. Tumor tissue including 1-3 mm peritumoral stroma, was mapped, manually micro dissected by surgical oral pathologist (RY) and scrapped out the slides, guided by one H&E stained section of each tumor. RNA extraction using Rneasy FFPE kit (Qiagen, catalog no 73504) was carried out in the Genomic Core Facility, university of Maryland Baltimore. RNA quality control (QC) analysis was run on nanochip, to ensure required 200nt in 50-300 ng with no prior amplification or enzymatic reaction. nCounter Human Pan Cancer IO-360 code set+panel standard cat #XT-CSPS-HIO360-12 and Master Kit-NAA-AKIT-012 platform was purchased from nanoString Technology (Seattle, WA). Hybridization was carried in a regular thermal cycler. The hybridized mix was purified using magnetic beads in the nCounter machine in the institute of genome sciences (IGS) University of Maryland Baltimore. Data analysis was carried using IO-360 platform 770 genes code sets using the nSolver 4.0 software basic and advanced custom analysis.

Statistical Analysis

The distribution of Sema4D and other scale variables were compared between groups of patients using non-parametric statistics, the independent-samples Mann-Whitney U test in case of two groups, and the independent-samples Kruskal-Wallis test in case of three or more groups. Associations between scale variables were quantified using Spearman's rank correlation coefficient, Rs, and tested against the null hypothesis of Rs=0. Categorical variables were summarized as frequency distributions with indication of the relative frequency and its 95% confidence limits in parenthesis when relevant. All p-values are two-tailed; statistical significance was called for p<0.05. A Bonferroni correction was applied to adjust for multiple comparisons, whenever relevant. Box-and-whisker plots were generated as a non-parametric representation of the distribution of a scale variable in a group; the sides of the box indicate the 1st and 3rd quartile of the population distribution with a vertical bar indicating the median. The whiskers extend to 1.5 times the height of the box or, if no case has a value in that range, to the minimum or maximum values. In case of a normally distributed variable, approximately 95% or the data are expected to lie inside the whiskers. Outlying data outside this interval are marked with an asterisk. Binary logistic regression was used for multivariable analysis of patient- and disease-characteristics associated with having elevated sSema4D levels. Statistical analysis of patient engagement, and survey data was conducted using IBM® SPSS® Statistics for Windows, release 24.0.0 (IBM Corp., Armonk, N.Y., USA). nSolver 4.0 analysis uses the student T-test with statistical significance $p<0.05$.

Example 2

Histological Inflammatory Subtypes Scored Using Sema4D in HNSCC

Histological patterns of tumor inflammation were described using immunoscore of T cell infiltration in the tumor microenvironment (7, 11). Sema4D is an immune biomarker that may be informative of the global immune contexture and hence facilitate visualization of all leukocytes in the tumor core and peritumoral stroma (11, 21, 22, 25, 32). To describe the pattern of histological inflammatory subtypes (HIS) in the current HNSCC cohort, IHC was performed to assess Sema4D levels on 104 HNSCC that were treated with surgical excision as the initial line of treatment (FIG. 1 sSema4D; soluble Sema4D, IHC; immunohistochemistry, HIS; histological inflammatory subtype, TIS; IFN-γ tumor immune signature, DGE; differential gene expression, IO-360; Immuno-Oncologic 770 gene set. HsS4D; high soluble Sema4D in plasma). The Sema4D positive IC infiltrate was examined in the invasive tumor front, peritumoral stroma, and tumor core. Eight cases of oral SCC were excluded due to lack of peritumoral stroma. The patients' demographics and tumor characteristics are described in Table 1. Sema4D showed moderate to strong membranous and cytoplasmic staining of the immune cells (IC). In the tumor cells (TC), Sema4D showed membranous and/or cytoplasmic staining that ranged from negative/weak to moderate/strong staining. The IC infiltration into the tumor islands was observed in 50 tumors (52%) that were scored as inflamed HIS (HIS-INF) (FIGS. 2A-2B). ICs infiltration mainly at the tumor invasive front, or between the tumor islands, but excluded by a thin peri-tumoral fibro-myxoid/fibrous rim, was a discriminatory factor to score as immune excluded (HIS-IE). This was observed in 38 cases (40%) (FIGS. 2B-2C). The stroma was almost deserted of IC infiltrate in 8 cases (8%) and was scored as histologically immune deserted (HIS-ID) (FIGS. 2E-2F).

TABLE 1

HNSCC Patients demographics and correlation with sSema4D in blood

| HNSCC | N (%) 104 (100%) | Correlation to sSema4D in plasma p-value |
|---|---|---|
| Age, median (IQR) | 67 (60, 73) | 0.32 |
| Gender | | |
| Females | 44 (42%) | 0.17 |
| Males | 60 (58%) | |
| Race | | |
| African American | 7 (7%) | 0.021$ |
| Caucasian | 88 (84%) | |
| Hispanic | 2 (2%) | |
| Asians | 7 (7%) | (−) 0.008ϕ |
| Location | | |
| Oral and mobile Tongue | 97 (93%) | 0.15 |
| Oropharynx | 7 (7%) | |
| Stage # | | |
| CIS | 3 (2%) | 0.29 |
| I | 35 (34%) | |
| II | 11 (10%) | |
| III | 10 (9%) | |
| IV | 45 (45%) | |
| PATH grade | | |
| CIS/Sup inv | 7 (7%) | 0.34 |
| well | 47 (46%) | |
| mod | 39 (38%) | |
| poorly | 10 (9%) | |
| HPV | | |
| Yes | 4 (4%) | 0.046 |
| No | 100 (96%) | |
| Smoking | | |
| Yes | 43 (41%) | 0.103 |
| No | 61 (59%) | |
| Alcohol | | |
| Yes | 19 (18%) | 0.70 |
| No | 85 (82%) | |
| History of dysplasia or HNSCC | 57 (63%) | |
| No history | 5 (6%) | 0.01# |
| History of Dysplasia | 28 (31%) | |
| History of HNSCC | | |

Decimals are rounded to the nearest whole number.
AJCC 8th edition staging system, only significant p values for the HNSCC racial groups are mentioned.
Caucasian versus African Americans$ and Caucasian versus Asianϕ.
HPV +ve: 1 oropharyngeal and 3 oral SCC.
HNSCC patients with history of dysplasia showed less level of sSema4D in plasma compared to other HNSCC groups.

Example 3

The Sema4D HIS Validated Using IFN-γ Tumor Immune Signature

Figure 3A:
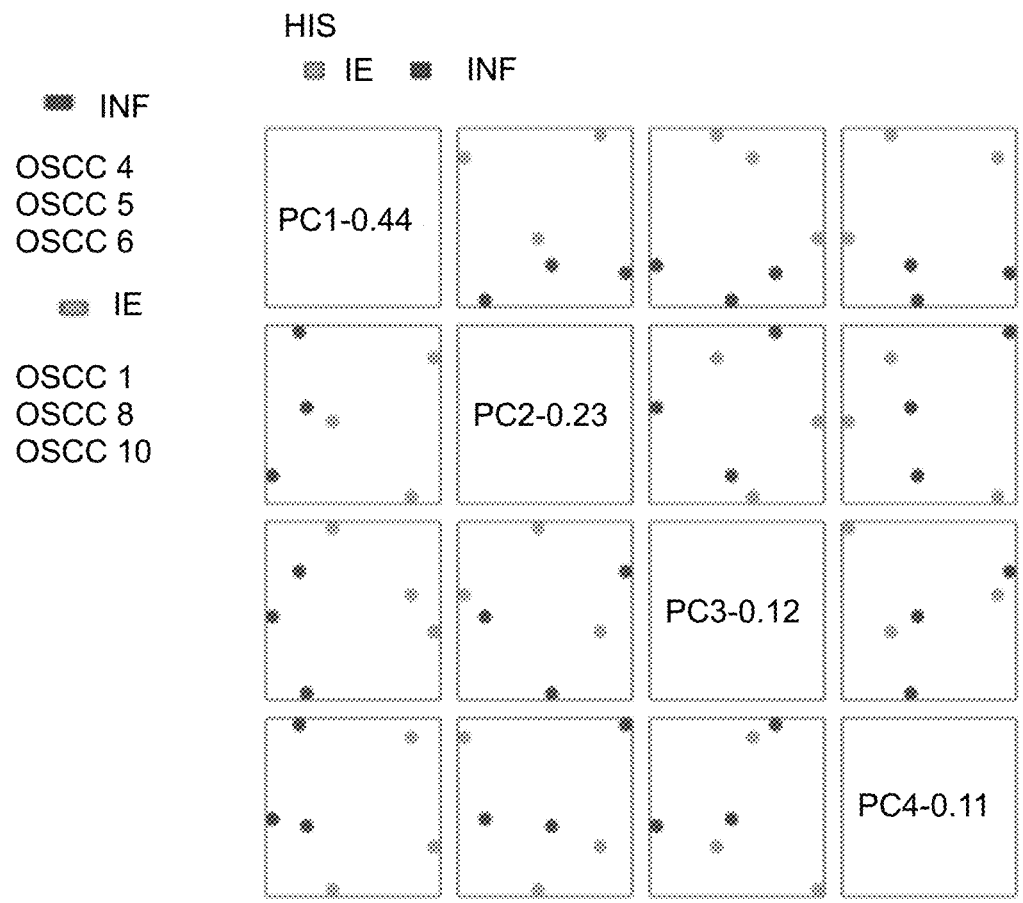
FIGS. 3A-3C are validations of the Sema4D HIS subtypes using principal component analysis (PCA) and IFN-γ signature on nSolver 4.0 analysis.
Figure 3B:
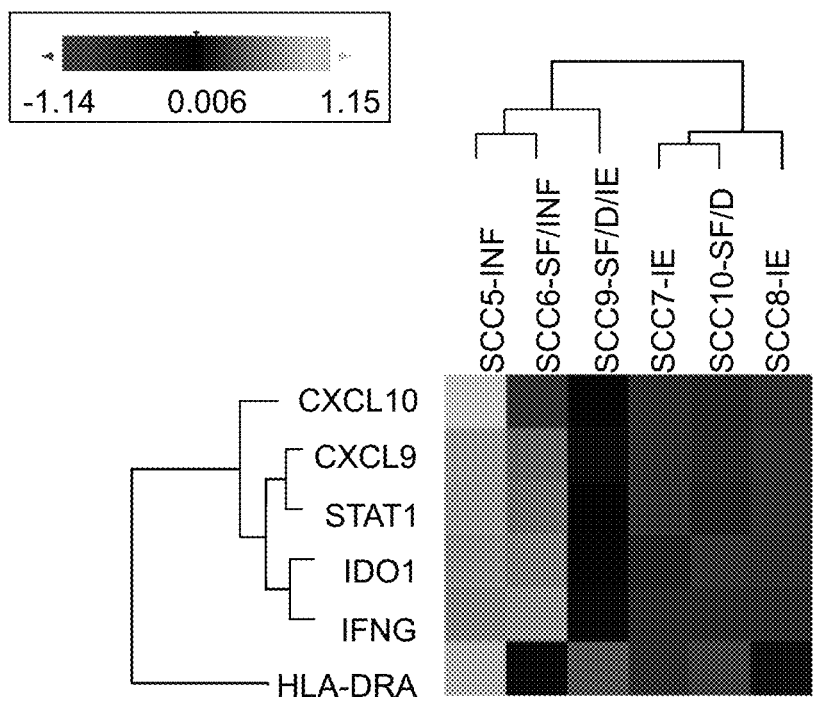
Figure 3C:
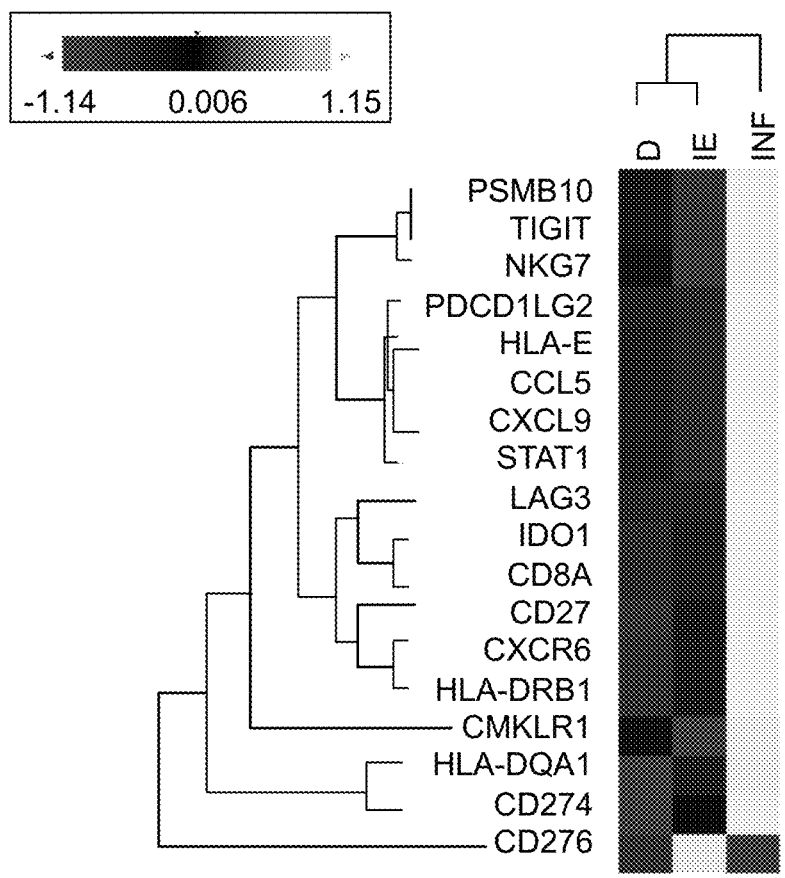
Figure 4A:
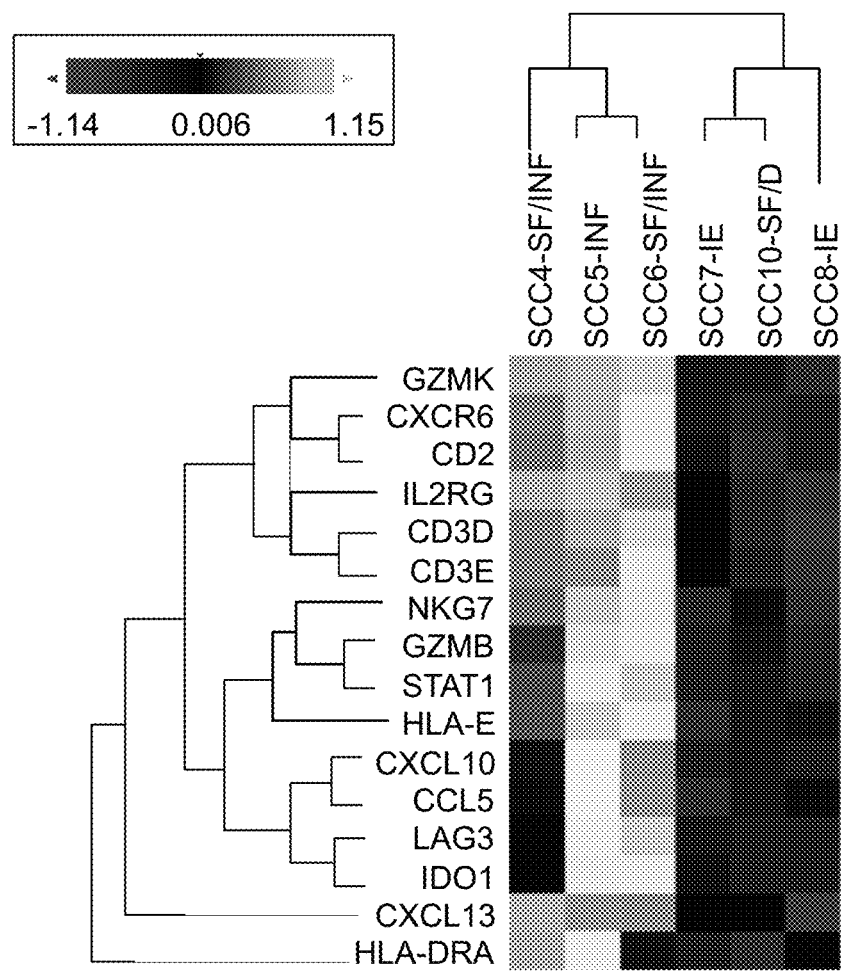
FIGS. 4A-4B is a heat map analysis of the HIS subtypes using expanded IFN-γ signature.
Figure 4B:
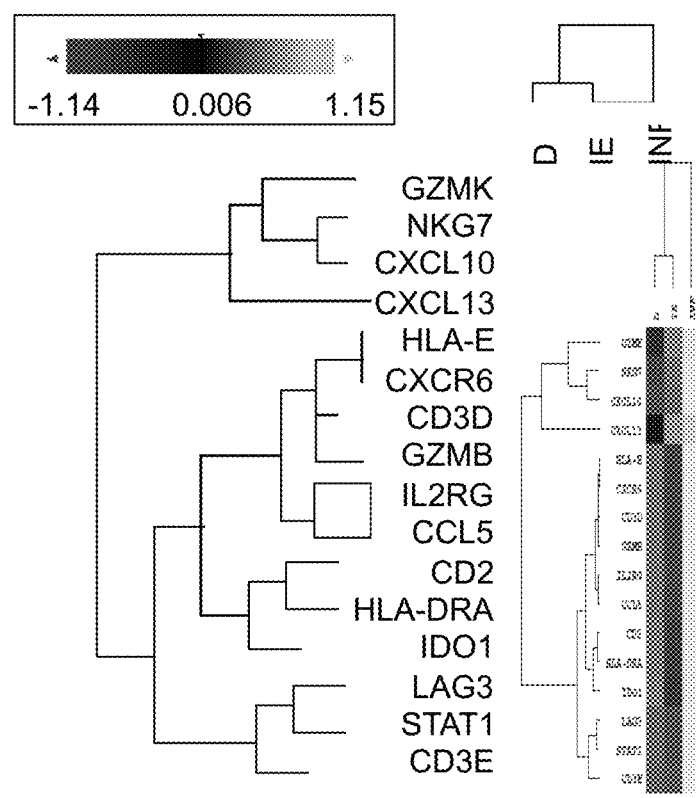

To validate the Sema4D HIS immune score, representative samples were tested using n Solver 4.0, principal component (PC) analysis. Indeed, the HIS-IE and HIS-INF, segregate on PC.1 (FIG. 3A). Next, the underlying immune transcriptional profile was examined using the T cell inflamed immune signature, composed of active IFN-γ signaling, cytotoxic effector and antigen presentation molecules, and T cell active cytokines that were previously sequentially validated to predict response to standard immunotherapy in HNSCC, as well as other tumor types (15). The refined 6 gene tumor immune signature (IDO1, CXCL10, CXCL9, HLA-DRA, STAT1, IFNG) was carried on a sample of cases representative of the Sema4D HIS subtypes using basic nSolver analysis (FIG. 3B). The expanded IFN-γ 16 gene signature (CD3D, IDO1, CD3E, CCL5, GZMK, CD2, HLA-DRA, CXCL13, IL2RG, NKG7, HLA-E, CXCR6, LAG3, CXCL10, STAT1, GZMB) was also run on individual samples and on grouped samples. Furthermore, the final validated T cell inflamed 18 gene signature (PSMB10, TIGIT, NKG7, PDCD1LG2, HLA-E, CCL5, CXCL9, STAT1, LAG3, IDO1, CD8A, CD27, CXCR6, HLA-DRB1, CMKLR1, HLA-DQA1, CD274, CD276) (15), was carried out on grouped samples representative of the three HIS subtypes (FIG. 3C). Interestingly, Sema4D HIS-INF tumors showed a positive IFN-γ 6 gene signature, and the HIS-IE and HIS-ID were negative for the IFN-γ 6 gene signature (FIG. 3B). The same distribution was observed using the expanded 16 gene (FIGS. 4A-4B) and the final validated IFN-γ 18 gene signature (FIG. 3C) (15).

Example 4

Sema4D in Peripheral Blood of HNSCC Patients

Figure 5A:
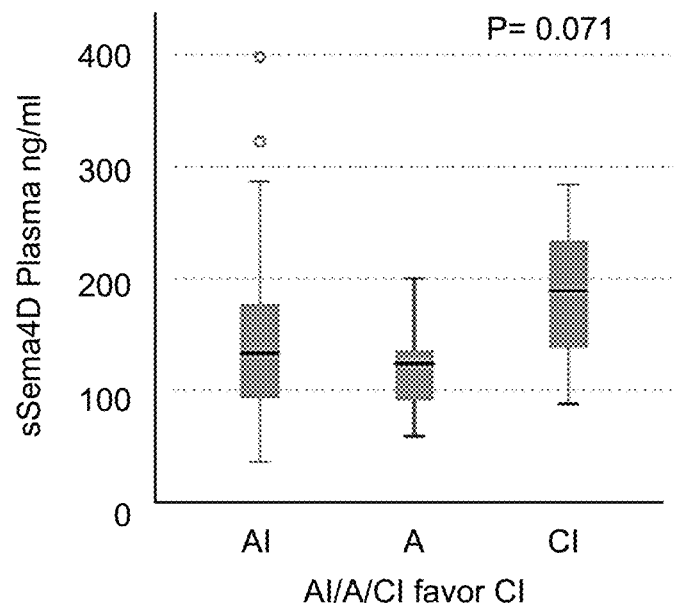
FIGS. 5A-5B are box and whisker plots for Independent-Samples Kruskal-Wallis test illustrating sSema4D in plasma.
Figure 5B:
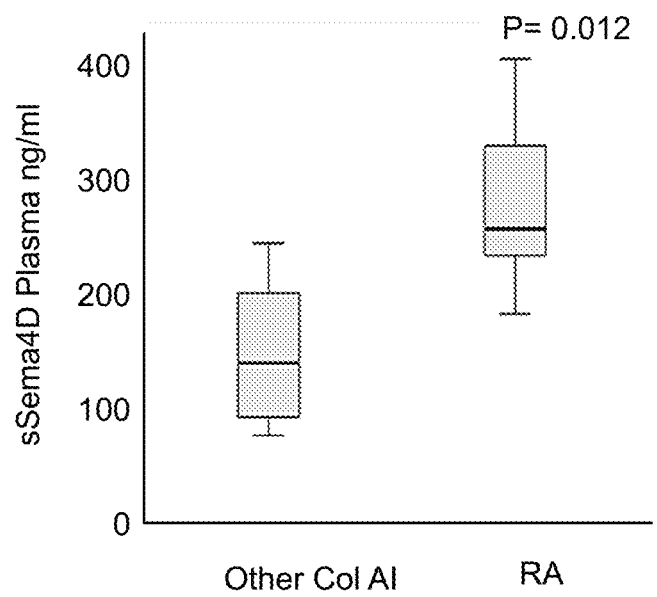

High levels of sSema4D (HsS4D) have been described in chronic inflammatory conditions like osteoarthritis (OA), rheumatoid arthritis (RA), other autoimmune conditions (AI), and allergic reactions; like asthma (A) (38, 39). sSema4D was also previously described in plasma of HNSCC (5). To investigate the potential of sSema4D in peripheral blood as a soluble immune biomarker that can read the level of inflammation in HNSCC patients, the level of sSema4D in the plasma of the 104 HNSCC patients were compared to the control groups of healthy donors, AI, A, and OA patients (Table 2). The data showed that there was no statistically significant difference between sSema4D levels among the AI/NOA conditions (p=0.07). The level of sSema4D was highest within the Collagenous AI (Col AI) group (p=0.011), and in the RA group compared to other Col AI diseases (p=0.012) (FIGS. 5A-5B).

TABLE 2

Descriptive analysis of the AI/A/CI controls for sSema4D in plasma.

| Control Groups | | Number | sSema4D in Plasma Range (Average) |
|---|---|---|---|
| Auto-immune (AI) (31 cases) | Rheumatoid Arthritis (RA) | 5 | 176-398 (274) |
| | Lupus (L) | 5 | 84-238 (162.8) |
| | Scleroderma (SC) | 1 | 70 |
| | L, RA | 1 | 88 |
| | Multiple sclerosis (MS) | 6 | 59-287 (142.3) |
| | Crohn's | 7 | 53-141 (102.4) |
| | Sarcoidosis | 5 | 36-179 (101.8) |
| | Myasthenia gravis (MG) | 1 | 114 |
| Allergy (10 cases) | Asthma | 13 | 59-240 (138.2) |
| Chronic Inflam. (10 cases) | Osteoarthritis (OA) | 10 | 122-240 (182.4) |

Collagenous AI conditions: RA, L, SC.
Non collagenous AI conditions: MS, Crohn's, Sarcoidosis and MG.
3 allergy patients had osteoarthritis and 1 RA had osteoarthritis
sSema4D levels were significantly higher in the AI/A/OA group compared to HNSCC (p = 0.003, adj p = 0.009) and healthy donors (p < 0.001, adj p = 0.001).
There was no statistically significant difference observed between sSema4D level in healthy donors and HNSCC (p = 0.051, adjust p = 0.152).
However, 75% of HNSCC cases had higher sSema4D levels in plasma than the median of the healthy donors (above 83 ng/ml).
There was no statistically significant difference observed between sSema4D levels in plasma and other clinical or demographic characteristics including smoking or alcohol drinking (Table 1). The HPV +ve cases, and various racial groups were limited in number, which prevented conclusive results related to these variables in the current HNSCC cohort.

Figure 6A:
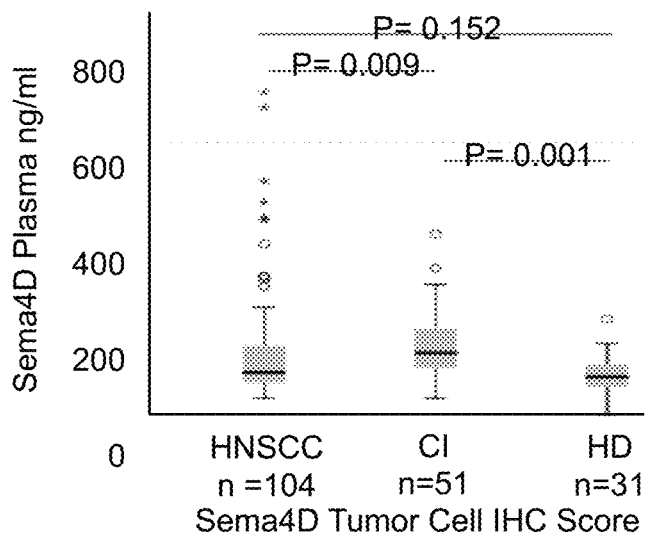
FIGS. 6A-6C are box and whisker plots for Independent-Samples Kruskal-Wallis test showing that sSema4D in plasma correlates with HIS-IE and Sema4D+ve tumor cells (TC) in real time.
Figure 6B:
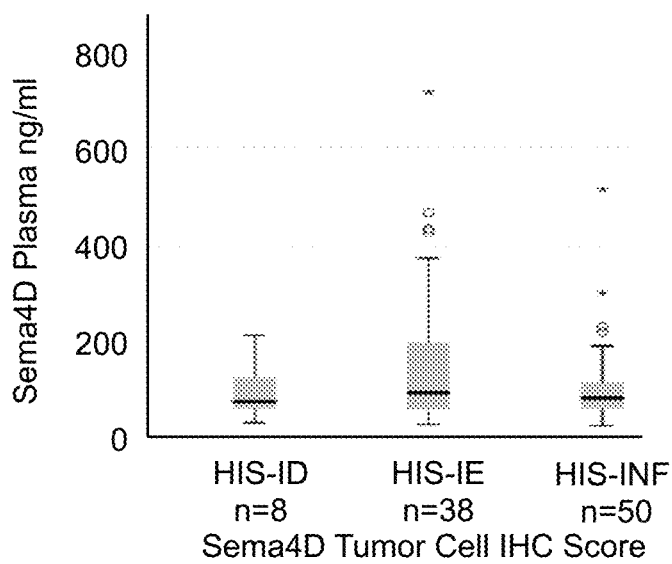

Example 5 sSema4D in Plasma Reads the Underlying HIS and Immuno-Oncologic Signature in HNSCC To investigate the potential of sSema4D as a soluble immune biomarker that can read the underlying tumor inflammatory stromal subtype, the level of sSema4D in plasma was analyzed with the paired tumor HIS subtype. The paired plasma and tumor tissue were collected at the same time point to allow for real time analysis (FIG. 1). Patients having a value exceeding 155 ng/ml (the 95th percentile of the levels measured in healthy donors) were scored as having elevated levels of sSema4D (HsS4D). Using this definition, 25.0% (95% CI, 16.7%-34.9%) of patients with HNSCC presented with elevated Sema4D (FIG. 6A) (Table 3). Our data showed a statistically significant association between HIS and HsS4D in plasma, P=0.007. This is driven by HIS-IE, where the proportion of cases with HsS4D is 42% with exact binomial confidence limits (26%, 59%) as compared with HIS-INF where 14% (6%, 27%) presented with HsS4D (FIG. 6B) (Table 4).

TABLE 3

Descriptive analysis of age, race, and sSema4D in plasma of HNSCC patients, AI/A/OA and HD

|  | HNSCC | AI/A/OA | HD |
|---|---|---|---|
| Number of cases | 104 | 51 | 31 |
| sSema4D in PLASMA | | | |
| Minimum | 36 | 36 | 0 |
| 25% Percentile | 69.25 | 102 | 59 |
| Median | 93 | 136 | 83 |
| 75% Percentile | 152.8 | 198 | 113 |
| Maximum | 712 | 398 | 211 |
| Range | 676 | 362 | 211 |
| Mean | 136.0 | 150.1 | 86.3 |
| Std. Deviation | 122.7 | 75.10 | 46.0 |
| Std. Error of Mean | 12.03 | 10.5 | 8.3 |
| Lower-upper 95% CI of mean | 112-160 | 129-171 | 69-103 |
| 95% CI of median | 96.10% | 95.11% | 97.06% |
| Lower-upper confidence limit | 87-110 | 122-152 | 65-109 |
| AGE | | | |
| Minimum | 21 | 19 | 18 |
| 25% Percentile | 60 | 41 | 25 |
| Median | 66.50 | 53 | 31 |
| 75% Percentile | 73 | 63 | 45 |
| Maximum | 93 | 83 | 66 |
| Range | 72 | 64 | 48 |
| Mean | 66.5 | 52.2 | 35.7 |
| Std. Deviation | 11.4 | 15. | 12.6 |
| Std. Error of Mean | 1.1 | 2.1 | 2.3 |
| 95% CI of median | 96.10% | 95.11% | 97.06% |
| Lower-upper confidence limit | 62-69 | 50 | 26 |
| RACE | | | |
| AA | 7 | 21 | 9 |
| Caucasian | 88 | 26 | 15 |
| Hispanic | 2 | 0 | 7 |
| Asian | 7 | 2 | 0 |
| AI | 0 | 0 | 0 |
| Others | 0 | 1 | 0 |
| AA, AI, Caucasian | 0 | 1 | 0 |
| GENDER | | | |
| Female | 44 | 36 | 14 |
| Male | 60 | 15 | 17 |

TABLE 4

HsS4D in plasma is associated with HIS-IE

| | | Plasma | | | |
|---|---|---|---|---|---|
| | | LsS4D | HsS4D | Total | p-value |
| HIS | ID | 7 | 1 | 8 | 0.007 |
| | | 87.5% | 12.5% | 100.0% | |
| | IE | 22 | 16 | 38 | |
| | | 57.9% | 42.1% | 100.0% | |
| | INF | 43 | 7 | 50 | |
| | | 86.0% | 14.0% | 100.0% | |
| | Total | 72 | 24 | 96 | |
| | | 75.0% | 25.0% | 100.0% | |

*HsS4D defined as sSema4D in plasma >155 ng/ml,
LsS4D; Low sSema4D,
ID; immune deserted,
IE; immune excluded,
INF; Inflamed.

Figure 6C:
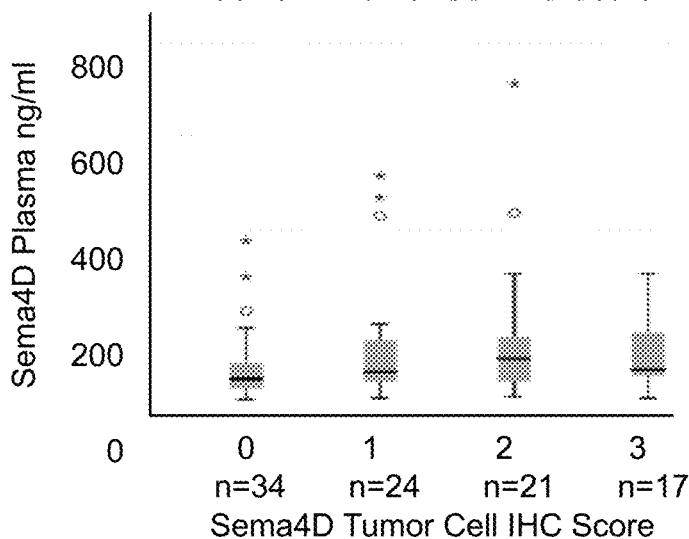

The tumor was scored for the Sema4D and PD-L1 in IC and TC. Interestingly, sSema4D levels in plasma correlated significantly with Sema4D$^{+ve}$ TC (p=0.018) (FIG. 6C) and PD-L1$^{+ve}$ IC (p=0.038). Furthermore, Sema4D$^{+ve}$ TC also correlated with PD-L1$^{+ve}$ IC (p=0.031). There was no statistically significant correlation observed between sSema4D and Sema4D in IC, PD-L1 in TC, nor PD-L1 or Sema4D CPS (Table 5).

TABLE 5

Sema4D and pd-l1 in tumor cell and immune cell in relation to sSema4D in plasma

| Sema4D in tumor | N (%) | correlation to sSema4D p-value |
|---|---|---|
| Sema4D TC | | |
| 0 | 34 (35%) | 0.018 |
| 1 | 24 (25%) | |
| 2 | 21 (22%) | |
| 3 | 17 (18%) | |
| TOTAL | 96 (100%) | |
| Sema4D IC | | |
| 0 | 6 (6.3%) | 0.243 |
| 1 | 5 (5.2%) | |
| 2 | 11 (11.5%) | |
| 3 | 74 (77.1%) | |
| TOTAL | 96 (100%) | |
| Sema4D CPS | | |
| 0 | 3 (3.1%) | 0.214 |
| 1 | 4 (4.2%) | |
| 2 | 10 (10.4%) | |
| 3 | 79 (82.3%) | |
| | 96 (100%) | |
| PD-L1 TC | | |
| 0 | 8 (8.4) | 0.249 |
| 1 | 7 (7.4) | |
| 2 | 12 (12.6) | |
| 3 | 68 (71.6) | |
| | 95 (100%) | |
| PD-L1 IC | | |
| 0 | 12 (13%) | 0.038 |
| 1 | 3 (3) | |
| 2 | 7 (7%) | |
| 3 | 74 (77%) | |
| | 96 (100%) | |
| PD-L1 CPS | | |
| 0 | 5 (5%) | 0.241 |
| 1 | 0 (1%) | |
| 2 | 3 (3%) | |
| 3 | 88 (92%) | |
| | 96 (100%) | |
| EXTENT OF INF | | |
| 0 | 3 (3%) | (−) 0.874 |
| 1 | 6 (6%) | |
| 2 | 37 (39%) | |
| 3 | 50 (52%) | |
| | 96 (100%) | |

Decimals are rounded to the nearest whole.
0; negative,
1; weak,
2; positive,
3; strongly positive.
Extent of inf; extent of inflammatory cell present independent of the pattern (INF or IE)

A multivariable logistic regression analysis was performed to identify patient-level factors associated with elevated HsS4D in patients with HNSCC. Patient-level factors tested in the model were age, gender, race, stage of disease, lympho-vascular invasion, smoking history, alcohol use, HIS, PD-L1 in IC, and PD-L1 in TC. Among these, HIS was highly statistically significant in the final model, P=0.0014 (Likelihood ratio test) in a model adjusting for PD-L1 in TC (P=0.035). The post-hoc test showed that most of the contrast related to HIS was between HIS-IE and HIS-INF, with an odds ratio for presenting with elevated sSema4D of 6.3 with 95% CI (2.2, 18.4), P=0.0007 for patients with HIS-IE tumors. This analysis suggests that the information on HIS conveyed by Sema4D is independent of PD-L1.

Figure 7:
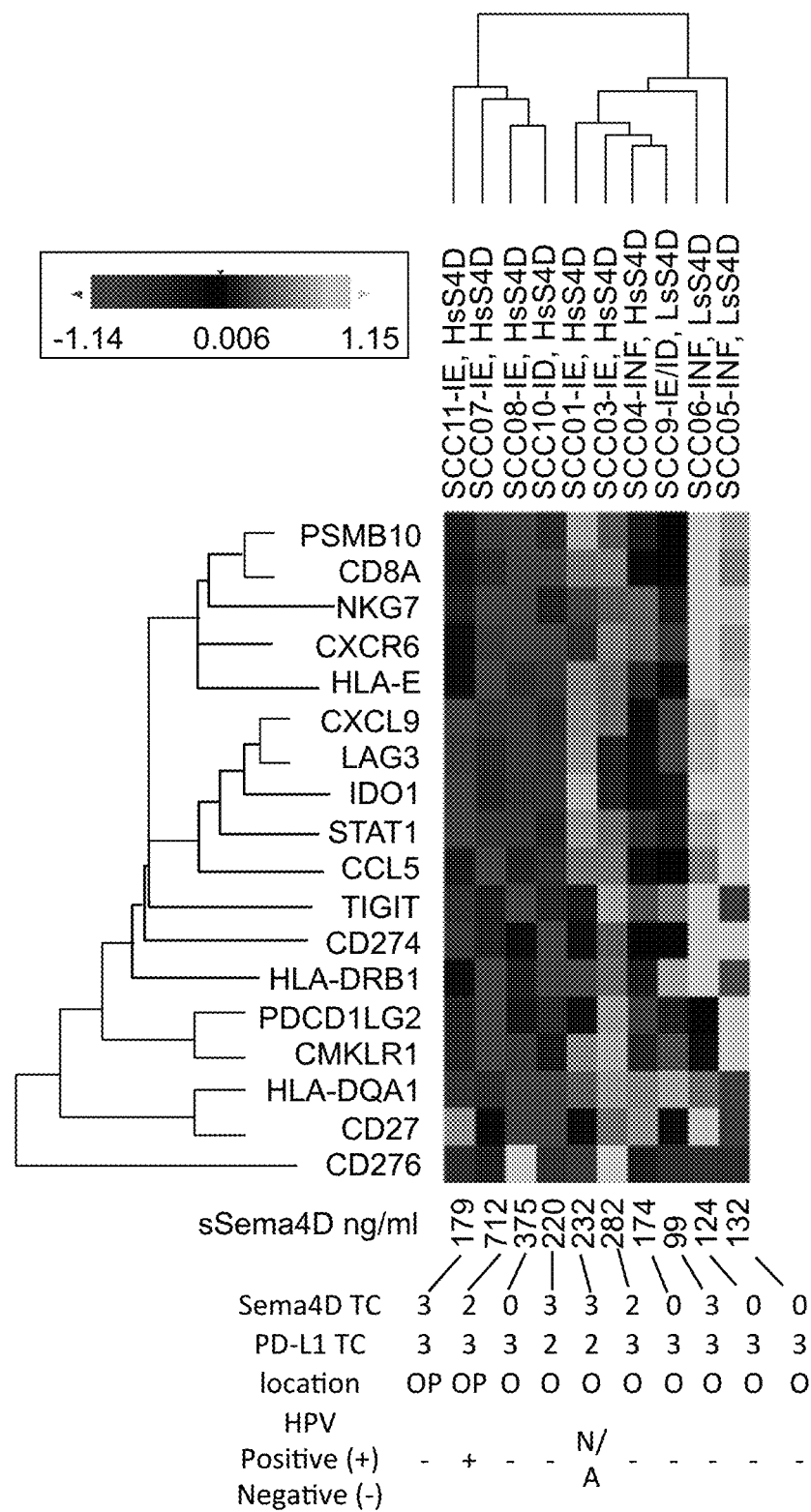
FIG. 7 is a heat map analysis of a tumor tissue samples (columns) for the IFN-γ 18 gene immune signature with corresponding HIS scoring and sSema4D levels in plasma.

Further the final 18 gene IFN-γ signature was analyzed in a sample of 10 cases in relation to the level of sSema4D in plasma, using basic nSolver 4.0 analysis. The 10 cases were selected to include replicates of the HIS patterns (INF versus IE &/or ID), and Sema4D+ve and -ve tumor cells. They were also selected to include replicates of Sema4D/PD-L1 co-positive tumor cells versus Sema4D-ve/PD-L1+ve tumor cells, as previously characterized (32) (FIG. 7). The reference cut off value>155 ng/ml for high sSema4D (HsS4D) in plasma was used. Four cases that were scored as HIS-IE, or HIS-ID revealed HsS4D in plasma and clustered as negative IFN-γ immune signature. On the other hand, two cases of HIS-INF, were LsS4D in plasma and clustered as positive IFN-γ signature. The remaining four cases represented a gray zone of IFN-γ expression, two of which were HIS-IE with a group of downregulated IFN-γ genes, and HsS4D in plasma that clustered more towards the positive IFN-γ signature. One case of HIS-IE with considerable number of downregulated IFN-γ genes, was LsS4D in blood and clustered towards IFN-γ positive. One case of the HIS-INF, with IFN-γ positive signature was HsS4D. Interestingly, this case had a group of downregulated IFN-γ genes (FIG. 7).

Figure 8:
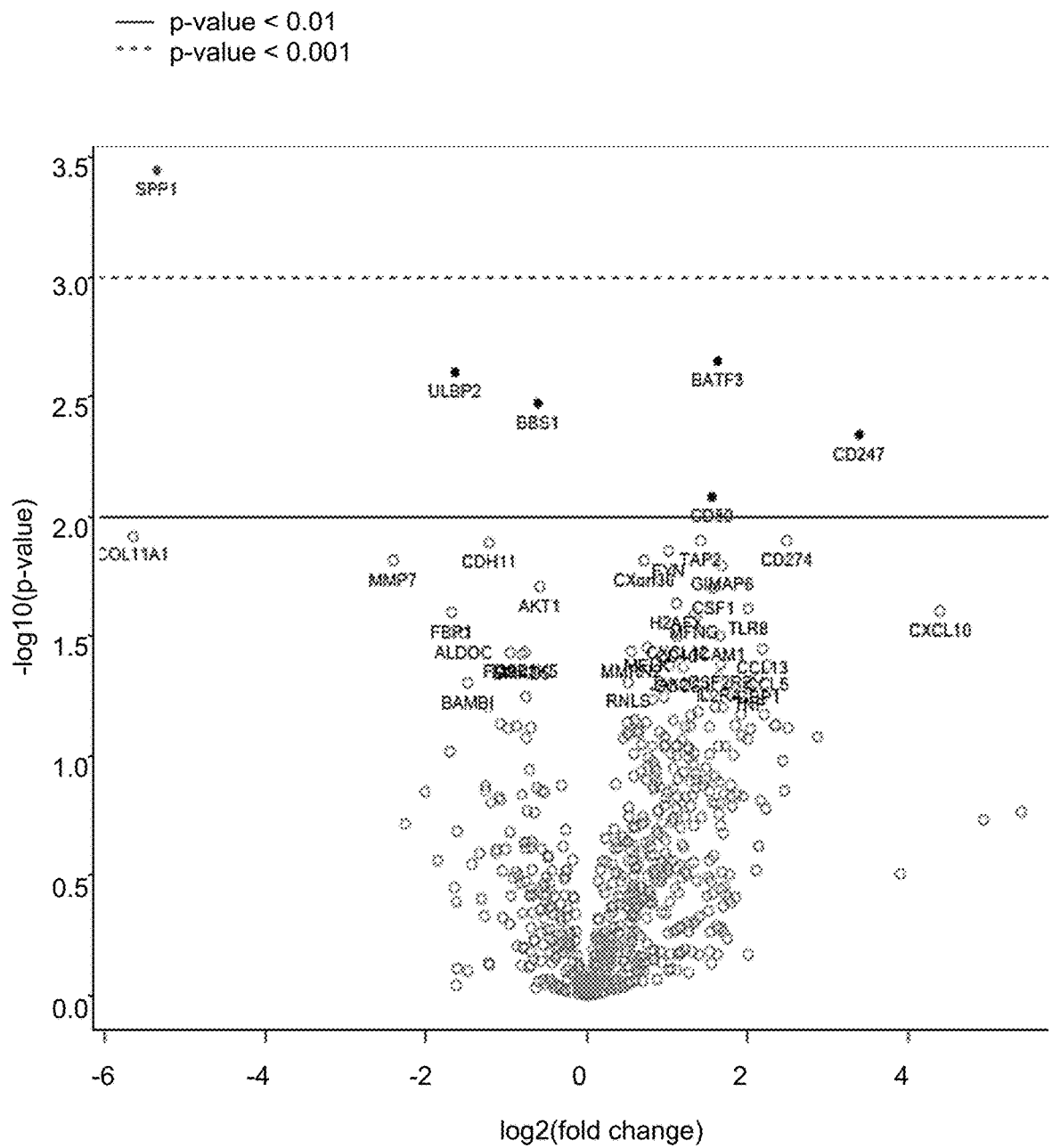
FIG. 8 shows an immuno-oncologic analysis of HNSCC tumor tissue using sS4D as a predictor variable using an DGE Volcano plot, presenting linear regression of 770 genes using 10-360, in LsS4D versus baseline of HsS4D.
Figure 9A:
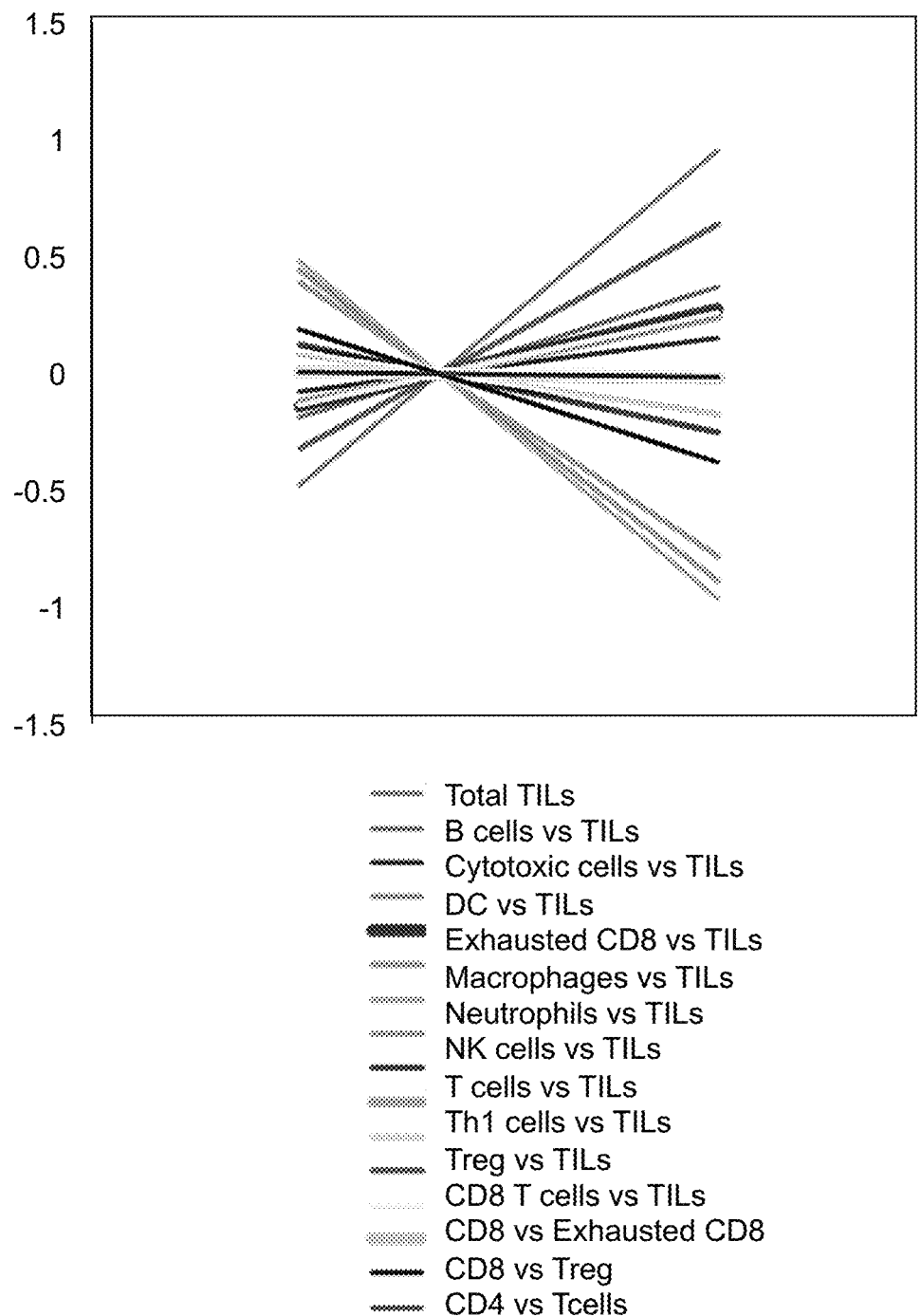
FIGS. 9A-9B is an immune cell type and immuno-oncologic pathways analysis versus sSema4D level in plasma.
Figure 9B:
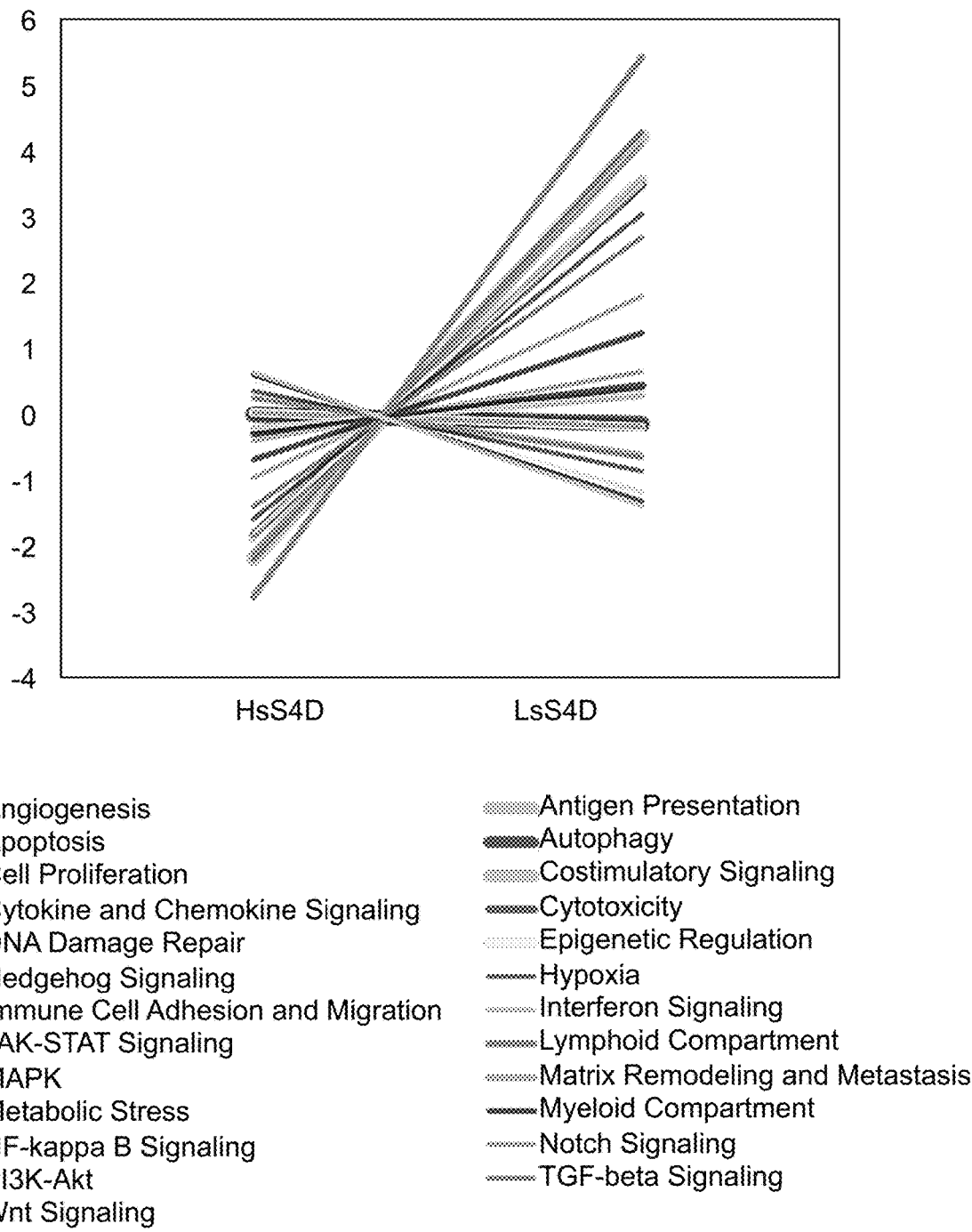

Finally, the underlying immune-oncologic profile of the HsS4D was compared to the LsS4D. 10-360, 770 genes were used as representative of the oncogenic pathways, tumor inflammation and tumor microenvironment. RNA was extracted from mapped FFPE tumor tissue. Using the sSema4D a predictor variable, with a customized, advanced nSolver analysis, differential gene expression of ~40 genes in LsS4D versus HsS4D was observed (FIG. 8 and Table 6). SPP1, ULBP2, COL11A1, and MMP7 were significantly upregulated in HsS4D compared to the LsS4D. The T cell inflamed tumor biomarker CD274 (PD-L1) was significantly upregulated in the LsS4D in addition to BATF3, CD247 (CD3ζ), CD80 among others (FIG. 8). The distribution of the IC type demonstrated total tumor infiltrating leukocytes (TILs) to predominate in LsS4D tumors (FIG. 9A). Analysis of the IC type relative to total TILs, showed Tregs to be the most numerous followed by B cells, exhausted T cells, then cytotoxic T cells in the LsS4D. Cytotoxic T cells were low in the LsS4D but were still higher than in HsS4D samples. Interestingly, the HsS4D had more mast cells, macrophages, and neutrophils in the TILs (FIG. 9B). A trend plot of the immune-oncologic signaling pathways showed that the highest was the lymphoid component, followed by costimulatory signaling, cytokines/chemokines, immune cell adhesion and migration pathways. IFN-γ, antigen presentation, and cytotoxicity pathways were also elevated. JAK-STAT and NF kappa B pathways were also among the upregulated pathways in the LsS4D compared to the HsS4D. In the HsS4D the Hypoxia and the Wnt signaling pathways were the most upregulated, followed by the Hedgehog pathway, metabolic stress, and TGF-β1 signaling (FIG. 9B). Taken together, these findings suggest that HsS4D in plasma reads the underlying non-inflamed tumor, hypoxic and metabolically stressed microenvironment.

Figure 10:
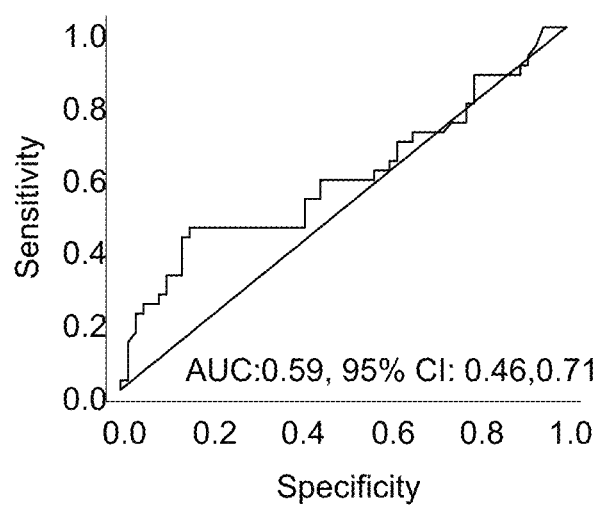
FIG. 10 is a sSema4D ELISA blood assay in HNSCC showing ROC curve of specificity and sensitivity of the HsS4D as a predictive marker of HIS-IE.

This biological association between Sema4D and HIS-IE raises the question whether Sema4D is of potential use as a predictive biomarker for the underlying tumor inflammatory stromal subtype. To this end, a receiver operating characteristic (ROC) curve analysis was performed. The area under the Receiver operating characteristic (ROC) curve for Sema4D as a predictor of HIS-IE was 0.59 with 95% CI (0.46, 0.71). This was not statistically significantly different from the null hypothesis of AUC=0.5, P=0.17. The sensitivity of elevated HsS4D for predicting HIS-IE was 42% with 95% CI (26%, 59%) and the specificity was 86% with 95% CI (74%, 73%) (FIG. 10).

TABLE 6

Immuno-oncologic analysis of HNSCC tumor tissue using the volcano plot in FIG. 8*.

| mRNA | Log2 fold change | P-value |
|---|---|---|
| SPP1 | −5.35 | 0 |
| BATF3 | 1.63 | 0.002 |
| ULBP2 | −1.64 | 0.003 |
| BBS1 | −0.607 | 0.003 |
| CD247 | 3.39 | 0.005 |
| CD80 | 1.56 | 0.008 |
| COL11A1 | −5.65 | 0.012 |
| TAP2 | 1.42 | 0.013 |
| CD274 | 2.49 | 0.013 |
| CDH11 | −1.21 | 0.013 |
| FYN | 1.02 | 0.014 |
| MMP7 | −2.41 | 0.015 |
| CXorf36 | 0.711 | 0.015 |
| GIMAP6 | 1.69 | 0.016 |
| AKT1 | −0.585 | 0.02 |
| CSF1 | 1.58 | 0.02 |
| H2AFX | 1.12 | 0.023 |
| TLR8 | 2.01 | 0.024 |
| CXCL10 | 4.4 | 0.025 |
| FBP1 | −1.68 | 0.025 |

*Top 20 significant DGE genes. Duplicates of LsS4D with IFN-γ +ve (SCC05, SCC06), were compared to HsS4D with IFN-γ -ve (SCC08 & SCC10) and HsS4D IFN-γ +ve (SCC01 and SCC04) (guided by FIG. 7).
DGE; differential gene expression,
LsS4D; low level of sSema4D in plasma,
HsS4D; high level of sSema4D in plasma.
P < 0.05 is significant.

The following references are cited herein:
1. Siegel et al. C A Cancer J Clin. 2020; 70(1):7-30.
2. Cohen et al. J Immunother Cancer. 2019; 7(1):184.
3. Bauml et al. J Clin Oncol. 2017; 35(14):1542-9.
4. Pak et al. Clin Cancer Res. 1995; 1(1):95-103.
5. Younis et al. J Immunol. 2016; 196(3):1419-29.
6. Butterfield L H. Semin Cancer Biol. 2018; 52(Pt 2):12-15.
7. Lechner et al. Oncotarget. 2017; 8(27):44418-33.
8. Feng et al. JCI Insight. 2017; 2(14).
9. Galon et al. Science. 2006; 313(5795):1960-4.
10. Galon et al. J Pathol. 2014; 232(2):199-209.
11. Galon J and Bruni D. Nat Rev Drug Discov. 2019; 18(3):197-218.
12. Cristescu et al. Science. 2018; 362(6411) doi:10.1126/science.aar3593.
13. Seiwert et al. Lancet Oncol. 2016; 17(7):956-65.
14. Cohen et al. Lancet. 2019; 393(10167):156-67.
15. Ayers et al. J Clin Invest. 2017; 127(8):2930-40.
16. Friedman C F and Postow M A. Curr Oncol Rep. 2016; 18(4):21.
17. Lousada-Fernandez et al. Int J Mol Sci. 2018; 19(6) doi: 10.3390/ijms19061704.
18. Lopez-Beltran et al. Front Oncol. 2018; 8:456.
19. Mamdani et al. Transl Lung Cancer Res. 2017; 6(6): 648-60.
20. Kolodkin et al. Cell. 1993; 75(7):1389-99.
21. Kumanogoh A and Kikutani H. J Cell Sci. 2003; 116(Pt 17):3463-70.
22. Delaire et al. J Immunol. 2001; 166(7):4348-54.
23. Hall et al. Proc Natl Acad Sci USA. 1996; 93(21):11785.
24. Bougeret et al. J Immunol. 1992; 148(2):318-23.
25. Delaire et al. Cell Mol Life Sci. 1998; 54(11):1265-76.
26. Kumanogoh et al. Immunity. 2000; 13(5):621-31.
27. Ishida et al. Int Immunol. 2003; 15(8):1027-34.
28. Basile et al. J Biol Chem. 2007; 282(9):6899-905.
29. Mou et al. Blood. 2013; 121(20):4221-30.
30. Motani K and Kosako H. J Biol Chem. 2018; 293(20): 7717-26.
31. Chabbert-de Ponnat et al. Int Immunol. 2005; 17(4): 439-47.
32. Derakhshandeh et al. Oncotarget. 2018; 9(13):11126-44.
33. Sierra et al. J Exp Med. 2008; 205(7):1673-85.
34. Chen et al. Asian Pac J Cancer Prev. 2013; 14(10):5883-90.
35. Cao et al. J Dermatol Sci. 2015; 79(2):127-36.
36. Ch'ng et al. Cancer. 2007; 110(1):164-72.
37. Lu Q. PLoS One. 2013; 8(5):e64265.
38. Yoshida et al. 2015; 67(6):1481-90.
39. Chapoval et al. Inflamm Res. 2017; 66(2):111-7.
40. Zhang et al. Hum Pathol. 2018; 82:104-12.
41. Huang et al. Cancer Manag Res. 2020; 12:8275-85.
42. Shen et al. Biomed Res Int. 2019; 2019:7376034.
43. Russell et al. Head Neck Oncol. 2013; 5(3):24.
44. Evans et al. Cancer Immunol Res. 2015; 3(6):689-701.
45. Clavijo et al. Cancer Immunol Res. 2019; 7(2):282-91.
46. Leonard et al. Mol Cancer Ther. 2015; 14(4):964-72.
47. Patnaik et al. Clin Cancer Res. 2016; 22(4):827-36.

What is claimed is:
1. A method for identifying and treating an inflammatory subtype of a head and neck squamous cell carcinoma in a subject in need thereof, comprising the steps of:
 a) obtaining a blood sample from the subject;
 b) quantitating a concentration of a soluble form of Semaphorin 4D (sSema4D) in the blood sample;
 c) identifying the head and neck squamous cell carcinoma as an inflamed subtype susceptible to a standard immu- notherapy when the concentration of sSema4D is below a threshold value of 155 ng/ml;
d) administering the standard immunotherapy to the subject;
e) repeating steps a to b during at least one interval of about every 3 weeks to about every 9 weeks; wherein:
the standard immunotherapy is continued if the concentration of sSema4D after each interval remains below 155 ng/ml; or
the standard immunotherapy is discontinued if the concentration of sSema4D after the interval is equal to or greater than 155 ng/ml.

2. The method of claim 1, wherein the quantitating step comprises performing an ELISA on the blood sample.

3. The method of claim 1, wherein the head and neck squamous cell carcinoma is an oral squamous cell carcinoma or an oropharyngeal squamous cell carcinoma.

4. A method for identifying and treating an inflammatory subtype of a head and neck squamous cell carcinoma, comprising the steps of:
a) obtaining a blood sample from a subject with a head and neck squamous cell carcinoma that is resistant to treatment with platinum containing therapeutics;
b) measuring a concentration of a soluble form of Semaphorin 4D (sSema4D) in the blood sample;
c) identifying the head and neck squamous cell carcinoma as an inflamed subtype susceptible to a standard immunotherapy when the concentration of sSema4D is below a threshold value of 155 ng/ml;
d) administering the standard immunotherapy to the subject;
e) repeating steps a to b during at least one interval of about every 3 weeks to about every 9 weeks; wherein:
the standard immunotherapy is administered if the concentration of sSema4D after each interval remains below 155 ng/ml; or
the standard immunotherapy is discontinued if the concentration of sSema4D after the interval is equal to or greater than 155 ng/ml.

5. The method of claim 4, wherein the cancer is a head and neck squamous cell carcinoma is an oral squamous cell carcinoma or an oropharyngeal squamous cell carcinoma.

* * * * *